(12) United States Patent
Lehoux et al.

(10) Patent No.: US 9,352,253 B2
(45) Date of Patent: *May 31, 2016

(54) SOLID/FLUID SEPARATION DEVICE AND METHOD FOR TREATING BIOMASS INCLUDING SOLID/FLUID SEPARATION

(71) Applicant: GREENFIELD SPECIALTY ALCOHOLS INC., Toronto (CA)

(72) Inventors: Richard Romeo Lehoux, Windsor (CA); Christopher Bruce Bradt, LaSalle (CA)

(73) Assignee: GREENFIELD SPECIALTY ALCOHOLS INC., Toronto (CA)

( * ) Notice: Subject to any disclaimer, the term of this patent is extended or adjusted under 35 U.S.C. 154(b) by 194 days.

This patent is subject to a terminal disclaimer.

(21) Appl. No.: 14/135,711

(22) Filed: Dec. 20, 2013

(65) Prior Publication Data

US 2014/0110324 A1    Apr. 24, 2014

Related U.S. Application Data

(62) Division of application No. 13/292,449, filed on Nov. 9, 2011, now Pat. No. 8,746,138.

(60) Provisional application No. 61/411,721, filed on Nov. 9, 2010.

(51) Int. Cl.
| | | |
|---|---|---|
| *B01D 25/12* | (2006.01) | |
| *D21C 7/00* | (2006.01) | |
| *B30B 9/16* | (2006.01) | |
| *B30B 9/26* | (2006.01) | |

(52) U.S. Cl.
CPC . *B01D 25/12* (2013.01); *B30B 9/16* (2013.01); *B30B 9/26* (2013.01); *B30B 9/267* (2013.01); *D21C 7/00* (2013.01); *Y02E 50/16* (2013.01)

(58) Field of Classification Search
None
See application file for complete search history.

(56) References Cited

U.S. PATENT DOCUMENTS

| | | | | |
|---|---|---|---|---|
| 3,230,865 | A | * | 1/1966 | Franz ................. B01D 29/0063 100/117 |
| 3,807,298 | A | | 4/1974 | Luke et al. |
| 4,340,184 | A | * | 7/1982 | Poss ....................... A22C 17/04 241/82.3 |
| 5,100,551 | A | | 3/1992 | Pall et al. |
| 5,333,556 | A | | 8/1994 | Isobe et al. |
| 5,417,155 | A | | 5/1995 | Tatsuzawa et al. |
| 5,515,776 | A | | 5/1996 | Scheucher et al. |
| 7,191,700 | B2 | | 3/2007 | Sasaki |

(Continued)

FOREIGN PATENT DOCUMENTS

| | | |
|---|---|---|
| CA | 1127552 | 7/1982 |
| CA | 2701407 A1 | 10/2010 |

(Continued)

OTHER PUBLICATIONS

International Patent Application No. PCT/CA2011/050695, Search Report dated Jan. 17, 2012.

(Continued)

*Primary Examiner* — Benjamin Kurtz
(74) *Attorney, Agent, or Firm* — Borden Ladner Gervals LLP; Mark Vickers

(57) ABSTRACT

A solid/fluid separation module and pretreatment apparatus and method enables pretreatment of biomass at high temperature and pressure with the ability to vary residence and processing times.

12 Claims, 9 Drawing Sheets

(56) References Cited

U.S. PATENT DOCUMENTS

| | | | |
|---|---|---|---|
| 7,347,140 | B2 | 3/2008 | Scheucher et al. |
| 7,357,074 | B2 | 4/2008 | Kraft et al. |
| 8,746,138 | B2 * | 6/2014 | Lehoux .................. D21C 7/00 100/117 |
| 2005/0199559 | A1 | 9/2005 | Duby |
| 2006/0037905 | A1 | 2/2006 | Sasaki |
| 2006/0288884 | A1 | 12/2006 | Babbini |
| 2009/0293742 | A1 | 12/2009 | Murphy et al. |
| 2013/0264264 | A1 * | 10/2013 | Lehoux ................ B01D 33/009 210/331 |

FOREIGN PATENT DOCUMENTS

| | | |
|---|---|---|
| CN | 201454229 | 5/2010 |
| CN | 102527128 | 7/2012 |
| CN | 202289634 | 7/2012 |
| DE | 102004037350 B3 | 4/2006 |
| EP | 0358837 A1 | 3/1990 |
| GB | 2005555 A | 4/1979 |
| GE | AP1996631 A | 6/1996 |
| JP | 58153509 | 9/1983 |
| JP | S59218298 A | 12/1984 |
| JP | 11253709 | 9/1999 |
| WO | 9014878 A1 | 12/1990 |
| WO | 9213710 | 8/1992 |
| WO | 02/14598 A1 | 2/2002 |
| WO | 2011102691 A2 | 8/2011 |
| WO | 2013/045091 A1 | 4/2013 |
| WO | 2013/183285 A1 | 12/2013 |

OTHER PUBLICATIONS

International Patent Application No. PCT/CA2013/050279, Search Report dated Jun. 14, 2013.
International Application No. PCT/CA2015/050491, International Search Report and Written Opinion dated Aug. 18, 2015.
International Application No. PCT/CA2015/050463, International Search Report and Written Opinion dated Aug. 19, 2015.
Georgian Application No. AP 2013 013600, Search Report dated Aug. 7, 2015.
Georgian Application No. AP 2013 013600, Documentary Conclusion dated Aug. 20, 2015.
Philippine Application No. 1-2013-500803, Exam Report dated Apr. 24, 2013.
U.S. Appl. No. 13/292,449, Office Action dated Sep. 9, 2013.
U.S. Appl. No. 13/292,449, Office Action dated Jan. 27, 2014.
U.S. Appl. No. 13/292,449, Notice of Allowance dated Apr. 7, 2014.
International Application No. PCT/CA2014/051132, International Search Report and Written Opinion dated Feb. 11, 2015.
English Translation of Colombian Patent Application No. 13-135295, Office Action dated Jul. 3, 3014.
European Patent Application No. 13772219.5; EESR dated Mar. 17, 2016.
U.S. Appl. No. 13/857,655, Notice of Allowance dated Apr. 1, 2016.

* cited by examiner

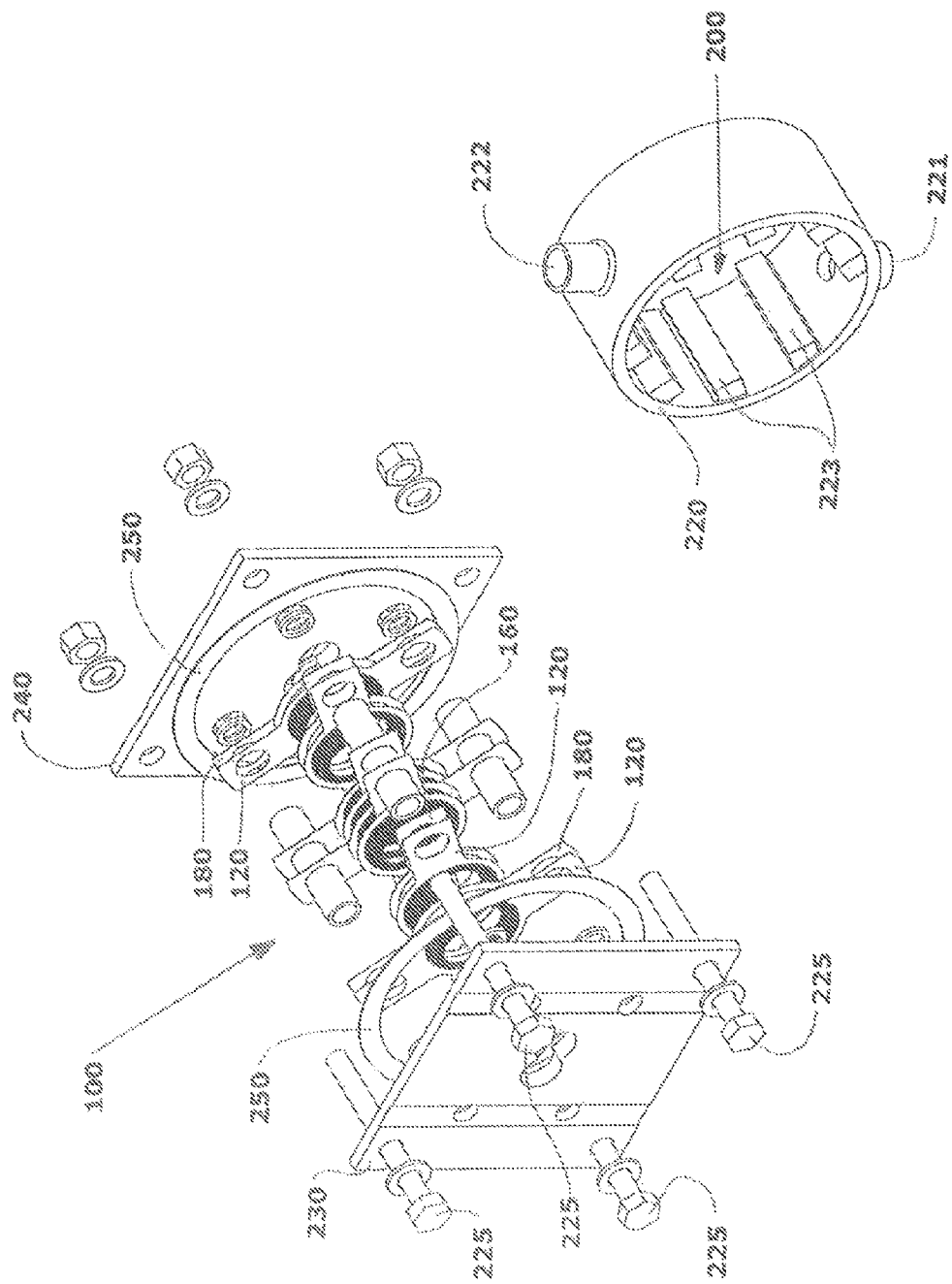

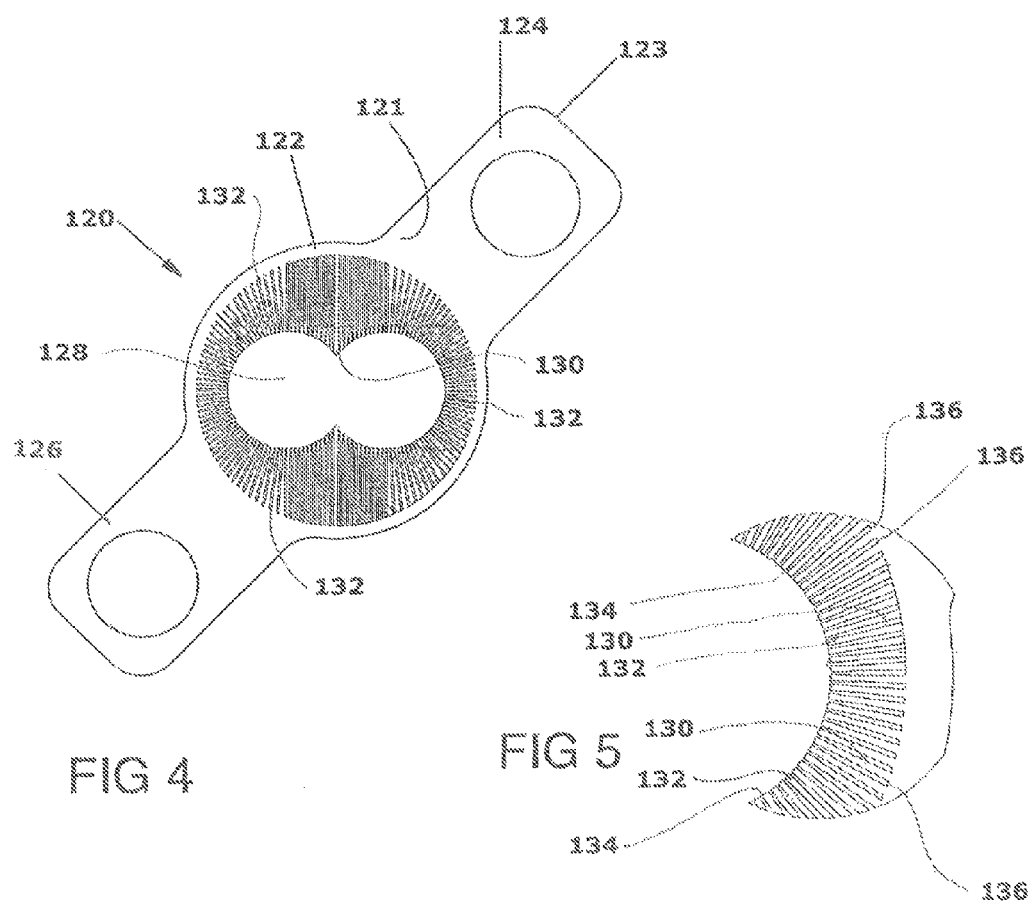

SOLID/FLUID SEPARATION DEVICE AND METHOD FOR TREATING BIOMASS INCLUDING SOLID/FLUID SEPARATION

CROSS REFERENCE TO RELATED APPLICATIONS

This application is a divisional of U.S. patent application Ser. No. 13/292,449 filed on Nov. 9, 2011, now U.S. Pat. No. 8,746,138, which claims priority to U.S. Provisional Patent Application No. 61/411,721 filed Nov. 9, 2010, both applications being expressly incorporated herein by reference in their entirety.

FIELD OF THE INVENTION

The present invention relates to a solid/fluid separation device and a method for the treatment of biomass including solid/fluid separation, more particularly, the pretreatment of a lignocellulose biomass in a biochemical conversion process.

BACKGROUND OF THE INVENTION

Pre-treatment of lignocellulose biomass for conversion to chemicals requires significant residence time, high pressure and high temperature. Liquids must be separated form the treated biomass at those conditions to achieve a high yield and process efficiency. Currently, multiple pieces of equipment are required to achieve this, which are costly in terms of capital and operating cost. Moreover, process efficiency is marginal.

A key component of process efficiency in the pretreatment of lignocellulosic biomass is the ability to wash and squeeze hydrolyzed hemi-cellulose sugars, toxins, inhibitors and/or other extractives from the solid biomass/cellulose fraction. It is difficult to effectively separate solids from liquid under the high heat and pressure required for cellulose pre-treatment.

During solid/fluid separation, the amount of liquid remaining in the solid fraction is dependent on the amount of separating pressure applied, the thickness of the solids cake, and the porosity of the filter. The porosity of the filter is dependent on the number and size of the filter pores. A reduction in pressure, an increase in cake thickness or a decrease in porosity of the filter, will all result in a decrease in the degree of liquid/solid separation and the ultimate degree of dryness of the solid fraction.

For a particular solids cake thickness and filter porosity, maximum separation is achieved at the highest separating pressure possible. For a particular solids cake thickness and separating pressure, maximum separation is dependent solely on the pore size of the filter.

High separating pressures unfortunately require strong filter media, which are able to withstand the separating pressure, making the process difficult and the required equipment very costly. When high separating pressures are required, the thickness of the filter media needs to be increased to withstand those pressures. However, to maintain the same overall porosity as the filter with the thinner filter media, thicker filter media require a larger pore size. This may create a problem, depending on the solids to be retained, since the acceptable pore size of the filter is limited by the size of the fibers and particles in the solids fraction, the clarity of the liquid fraction being limited solely by the pore size of the filter media. Pores that are too large allow a significant amount of suspended particles to collect in the liquid fraction, thereby reducing the liquid/solid separation efficiency.

Over time, filter media tend to plug with suspended solids reducing their production rate, especially at the high pressures required for cellulose pre-treatment. Thus, a backwash flow of liquid is normally required to clear a blockage and restore the production rate. Once a filter becomes plugged, it takes high pressure to backwash the media. This is particularly problematic when working with filter media operating at pressures above 1000 psig with a process that is to be continuous to maximize the production rate and to obtain high cellulose pre-treatment process efficiency. The current equipment required to effectively perform cellulose pre-treatment is both complex and expensive as there is no known equipment available for simultaneously carrying out multiple lignocellulosic biomass pretreatment steps in a single apparatus.

Conventional single, twin, or triple screw extruders do not have the residence time necessary for low energy pre-treatment of biomass, and also do not have useful and efficient solid/fluid separating devices for the pre-treatment of biomass. U.S. Pat. No. 7,347,140 discloses a screw press with a perforated casing. Operating pressures of such a screw press are low, due to the low strength of the perforated casing. U.S. Pat. No. 5,515,776 discloses a worm press and drainage perforations in the press jacket, which increase in cross-sectional area in flow direction of the drained liquid. U.S. Pat. No. 7,357,074 is directed to a screw press with a conical dewatering housing with a plurality of perforations for the drainage of water from bulk solids compressed in the press. Again, a perforated casing or jacket is used. As will be readily understood, the higher the number of perforations in the housing, the lower the pressure resistance of the housing. Moreover, drilling perforations in a housing or press jacket is associated with serious challenges when very small apertures are desired for the separation of fine solids. Thus, an improved dewatering module for a screw press is desired.

SUMMARY OF THE INVENTION

It is an object of the present invention to obviate or mitigate at least one disadvantage of previous solid and liquid separation devices and processes.

It is a further object to provide an improved method for the pre-treatment of lignocellulosic biomass and a liquid/solid separation module for improved separation performance at elevated separating pressures.

In order to improve solids/fluid separation, the invention provides a solid/fluid separation module for a screw press, the module separating fluid from a liquid containing mass of solids compressed by the screw press to pressures above 100 psig. The separation module includes a filter unit having a porosity of 5% to 40% (total pore area relative to the total filter surface). Preferably, the module withstands operating pressures of 3000 psig at a filter porosity of 5 to 40%, more preferably 11 to 40%. The filter unit preferably includes a plurality of filter pores with a pore size of 0.00005 to 0.005 square inch.

In a preferred embodiment, the filter unit includes filter pores having a pore size of 0.00005 square inch for the separation of fine solids, a porosity of 5.7% and a pressure resistance of 2,500 psig. In another embodiment, the filter unit includes pores having a pore size of 0.005 square inch and a porosity of 20% and a pressure resistance of 5,000 psig. In a further preferred embodiment, the filter unit includes pores of a pore size of 0.00005 square inch and a porosity of 11.4%. In still another preferred embodiment, the filter unit includes pores having a pore size of 0.005 square inch and a porosity of 40%. In still another embodiment, the filter unit includes pores of a pore size of 0.00003 square inch.

To achieve maximum solid/fluid separation efficiency, it is desirable to minimize filter pore size, while maximizing filter porosity and to operate at elevated separation pressures. Minimizing pore size is a challenge in conventional screw presses due to the need for cutting cylindrical passages into the filter jacket. This problem has now been addressed by the inventors. In the filter unit of the present invention, filter pores are formed by simply cutting a slot through a filter plate, which can be achieved much more easily than drilling holes in a pressure jacket. Using slots also allows for the creation of much smaller filter pores by using very thin filter plates and narrow slots. For example, by using a filter plate of 0.005 inch thickness and cutting a slot of 0.01 inch width into the filter plate, a pore size of only 0.00005 square inch can be achieved. Even smaller pore sizes can be achieved by using thinner filter plates, for example a plate of 0.003 inch thickness. Moreover, in order to provide a relatively high porosity at elevated operating pressures, a separation module is provided for sealing connection to a source of a pressurized mass of liquid containing solids, for example a screw press.

In one aspect, the separation module includes a pressurizable collection chamber and a filter unit for sealingly receiving the pressurized mass. The filter unit has a preselected filter pore size and a preselected porosity. The filter unit includes at least one filter plate having opposite front and back faces, a cover plate engaging the front face of the filter plate and a backer plate engaging the back face of the filter plate. The filter, cover and backer plates define a throughgoing core opening sealed from the collection chamber for receiving the pressurized mass. The filter plate has at least one throughgoing filter slot extending away from the core opening into the filter plate, the filter slot being sealed at the front and back faces by the cover and backer plates for forming a filter passage having the preselected filter pore size. The backer plate has a recess for defining together with the back face a drainage passage in fluid communication with the collection chamber and the filter passage. For increased porosity, the filter plate preferably includes a plurality of separate, filter slots for increasing the porosity of the filter unit and the drainage passage is in fluid communication with all the filter slots. To increase the porosity of the filter unit even further, the filter unit preferably includes multiple pairs of filter and backer plates arranged behind the cover plate in a stack of alternating filter and cover plates, whereby each backer plate sandwiched between two filter plates functions as the backer plate for one and the cover plate for the other filter plate. By alternating the filter and backer plates, the separating pressure capacity of the filter unit is increased. By using backer plates that are thicker than the filter plates, the pressure capacity of the filter unit can be further improved. Similarly by using backer and filter plates that are larger in diameter, the pressure capacity of the filter unit can be increased.

In one embodiment, the separation module is mountable to the barrel of a screw press and the core opening is sized to fittingly receive a portion of the extruder screw of the press. The extruder screw preferably has close tolerances to the core opening of the filter block for continually scraping the compressed material away from the filter surface while at the same time generating a significant separating pressure. In the event that a small amount of fibers become trapped on the surface of the filter, they will be sheared by the extruder elements into smaller pieces and ultimately pass through the filter and out with the liquid stream as very fine particles. This provides a solid/fluid separation device which allows for the separation of solid and liquid portions of a material in a high pressure and temperature environment.

In another aspect, the separating module for separating liquids or gases from a pressurized mass of liquid containing solids includes a sealable housing having a pressure jacket defining a collection chamber for liquids and gases; a liquid outlet and a gas outlet on the jacket for respectively draining liquids and gases from the collection chamber; an inlet end plate removably securable to an inlet end of the jacket; an outlet end plate removably securable to an outlet end of the jacket and at least one filter pack including a filter plate and a backer plate, the filter pack sandwiched between the inlet and outlet end plates; the filter and backer plates having an aligned core opening sealed from the collection chamber for receiving the pressurized mass, wherein the filter plate includes at least one throughgoing filter slot extending from the core opening into the filter plate and the backer plate defining a passage in fluid communication with the filter slot and the collection chamber.

Preferably, the sealable housing has two or more pairs of filter and backer plates.

Preferably, the filter plate includes a plurality of filter slots.

Preferably, each backer plate includes a circular groove in fluid communication will all filter slots of an adjacent filter plate.

Preferably, each of the filter and backer plates has a pair of opposite mounting tabs for alignment and interconnection of the plates. Each mounting tab may have a hole for receiving a fastening bolt, for alignment and clamping together of the stack of filter and backer plates in a continuous filter block. Alternatively, the hole for the fastening bolt is omitted and the pressure jacket includes ridges on an inner surface for aligning the tabs and preventing rotation of the filter and backer plates relative to the core opening.

In a further aspect, the present disclosure provides a use of the solid/fluid separating module as described for the processing of a material having a solid portion, a liquid portion and gas portion, to separate the solid portion from the liquid and gas portions.

In a further aspect, the present invention resides in a process for pretreating biomass, in particular lignocellulosic biomass.

Other aspects and features of the present disclosure will become apparent to those ordinarily skilled in the art upon review of the following description of specific embodiments in conjunction with the accompanying figures.

BRIEF DESCRIPTION OF THE DRAWINGS

For a better understanding of the embodiments described herein and to show more clearly how they may be carried into effect, reference will now be made, by way of example only, to the accompanying drawings which show the exemplary embodiments and in which:

FIG. 3 shows an exploded view of the solid/fluid separation module shown in FIG. 2;

FIG. 4 shows a filter (finger) plate of the separation module having narrow filter slots as drainage channels;

FIG. 5 shows an enlarged detail view of the filter (finger) plate of FIG. 4;

DETAILED DESCRIPTION OF THE PREFERRED EMBODIMENTS

Figure 1:
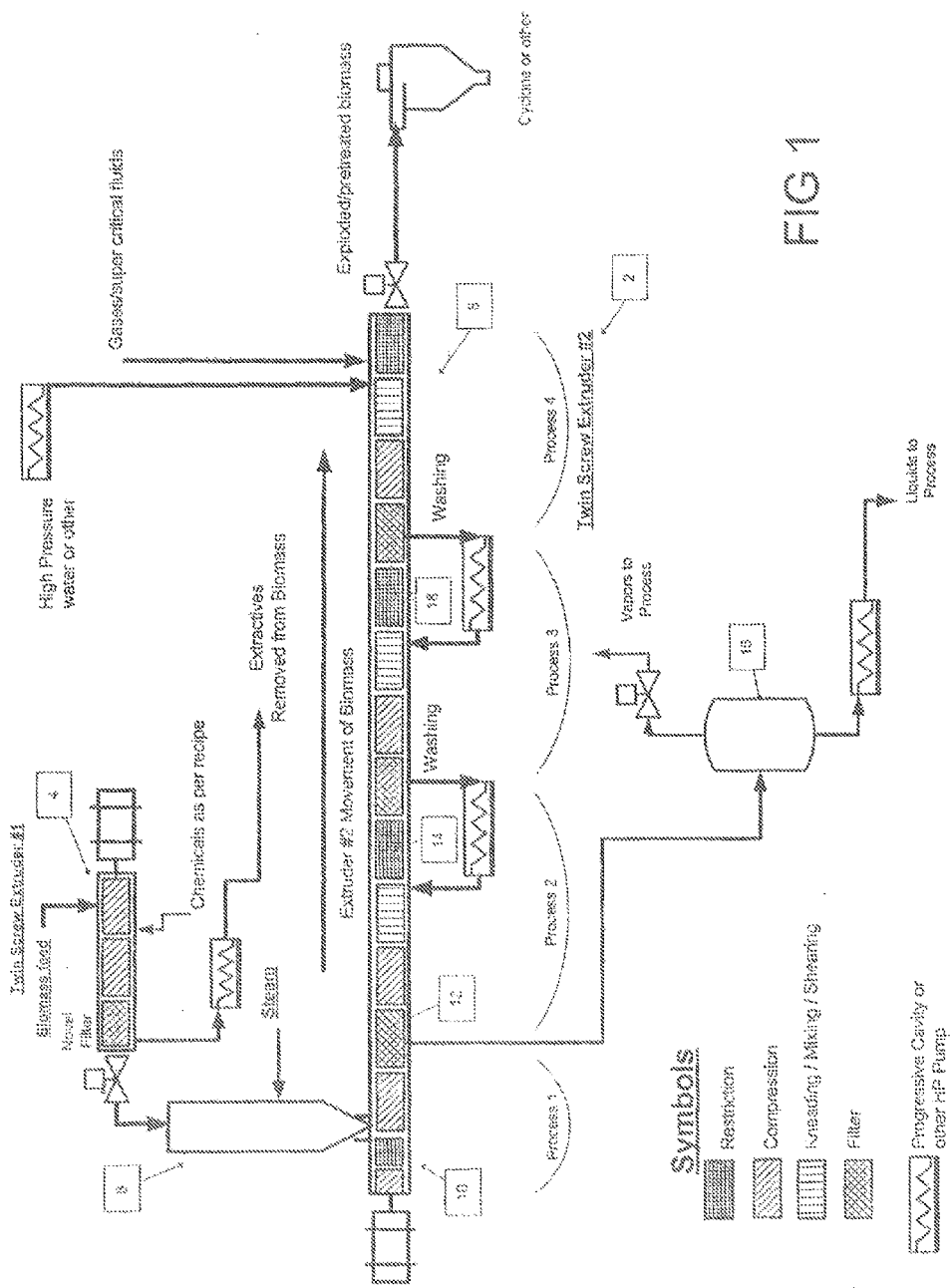
FIG. 1 shows a schematic view of a cellulose pre-treatment apparatus incorporating a twin screw extruder with solid-liquid separation module.

It will be appreciated that for simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

As shown in FIG. 1, a simple continuous cellulosic ethanol pre-treatment system 2 of the present invention consists of only three machines. A first extruder 4 being used as a continuous high pressure plug feeder/mixer for biomass. The extruder 4 feeds the biomass into a vertical reactor 6. The vertical reactor 6 is capable of having a long residence time. The vertical reactor 6 feeds the biomass into a second extruder 8, preferably a twin screw extruder. The pre-treatment process comprises flowing the biomass through the first extruder 4, the vertical reactor 6, and the second extruder 8.

The extruder 4, which may also be a twin screw extruder, is used to provide a continuous feed into the pressurized vertical reactor 6. Mixing of various chemicals in the extruder 4 is possible depending on the type of feedstock. The extruder 4 has an automatic valve, which closes upon loss of feed to prevent loss of pressure in the case of loss of feedstock.

Vertical Reactor 6 is capable of operating with various chemicals at pressures of up to 350 psig and temperatures of up to 425° F. (220° C.) depending on the biomass. Residence time in the vertical reactor 6 can be varied from a few minutes to many hours depending on the biomass.

The partially treated biomass is discharged from the vertical reactor 6 into the second extruder 8 at a pressurized feed zone 10. In the second extruder 8, most of the solid biomass moves to an output end (right side in FIG. 1), and a small fraction is conveyed backward to create a pressure seal on the drive shafts. In the second extruder 8, higher pressures are generated than in the first reactor, as required by various biomasses and the pre-treatment process is completed by two, three or more separate processes depending on the biomass.

Wash liquid (water, ammonia or other) moves counter or co-current to the flow of solids biomass (left in FIG. 1) such that the biomass is washed with the cleanest liquid at the end of the extruder. Gases or super critical fluids such as carbon dioxide can be injected at the output end to improve explosive force as required depending on the biomass treated. At the output end various extruder screws, and/or another reactor vessel, and/or a control valve and/or a rotating orifice can be used to create a dynamic seal and explosive force required by different types of biomass at different pressures and dry matter content. Upon explosive expansion of the biomass from one of these devices at the output, a cyclone or other separating device is used to collect both the solids and any gases, which are ejected.

Upon entering the second extruder 8, most of the biomass is conveyed forward while a small amount is conveyed backward to create a dynamic pressure seal to prevent leakage from the vertical reactor 6. The biomass enters process stage 1, as shown on FIG. 1, and is subjected to a higher pressure, high temperature initial counter current filtration zone using a first solid/fluid separation device 12 as will be described in more detail below with reference to FIGS. 2 to 13. At this point, some biomass only requires squeezing of extractives and hemicellulose syrup and may not require wash water. In the solid/fluid separation device, liquid hemicellulose syrup and or extractives are removed with controlled cake thickness by the use of various screw elements. Permeability, pore size, filter area and pressure rating is controlled by using different filter plate designs, depending on the biomass type treated. Liquid pressure and flashing are controlled by the use of a pressure controlled flash tank 16.

Upon exiting the first solid/fluid separation device 12, the biomass is conveyed forward (to the right in FIG. 1) and heated with the use of steam/high pressure water from the forward area and pressure through compression/conveying with various screw elements is applied. In process stage 2 shown in FIG. 1, the biomass is subjected to high pressure mixing/kneading with variable shear energy for various biomasses to improve pre-treatment. High pressure, high temperature final counter current filtration (can only squeeze partial hemicellulose syrup and extractives and not counter current wash as required by some types of biomass) of liquid hemicellulose occurs with controlled cake thickness by the use of various screw elements. Permeability, pore size, filter area and pressure rating are controlled by selecting filter plates of appropriate design in a second solid/fluid separating device 14 depending on the biomass type treated. Liquid pressure and flashing is controlled by the use of a pressure controlled flash tank 16.

In process stage 3, the biomass is subjected to heat and pressure through compression/conveying with various different extruder screw elements. Shear energy is imparted to the biomass to improve enzyme accessibility as required to improve the pre-treatment of various biomasses. High pressure mixing/kneading of biomass with variable shear energy for various biomasses is used to improve pre-treatment. High pressure, high temperature mid-cycle (or final cycle, depending on biomass) can be imparted using counter or co-current filtration of liquid hemicellulose syrup with controlled cake thickness by the use of various screw elements. Permeability, pore size, filter area and pressure rating are controlled by selecting appropriate filter plates in a third solid/fluid separator 18 to suit biomass properties. Liquid pressure and flashing are controlled by the use of the pressure controlled flash tank 16.

In process stage 4 shown in FIG. 1, the biomass is subjected to heat and pressure through compression/conveying with various extruder screw elements. High pressure mixing/kneading of biomass with variable shear energy is selectable for various biomasses. In process stage 4, the biomass is mixed with high pressure water or other fluids/solutions for the final washing stage. Other fluids can include molecules, which are a gas at room temperature such as high pressure liquid $CO_2$, which will become super critical within the extruder due to higher temperature or ammonia which will be a high pressure gas.

The solid fibrous biomass is then conveyed under the highest pressure of the system through the second extruder 8 and one of the dynamic seal alternatives and exits under a controlled explosive decompression of compressed gases such as steam, ammonia or super critical fluids within the fibers at the outlet of the twin screw extruder into a solid/gas separating device (cyclone or other). When high pressure liquid $CO_2$ is used, the super critical nature of this fluid when it gets heated by the biomass permeates the internals of the solid fibers similar to a gas and results in a partial flow of the fluid upstream against the solids pressure profile just as a gas does. This super critical fluid within the fiber exerts an explosive force from within most fibers many times greater than a standard gas upon exiting the extruder through the dynamic seal, modifying the solid cellulose particles and thereby increasing enzymatic accessibility. Also at the discharge of the twin screw is an automatic control valve, which is used to keep the system somewhat pressurized should there be a loss of feed or power.

Figure 2:
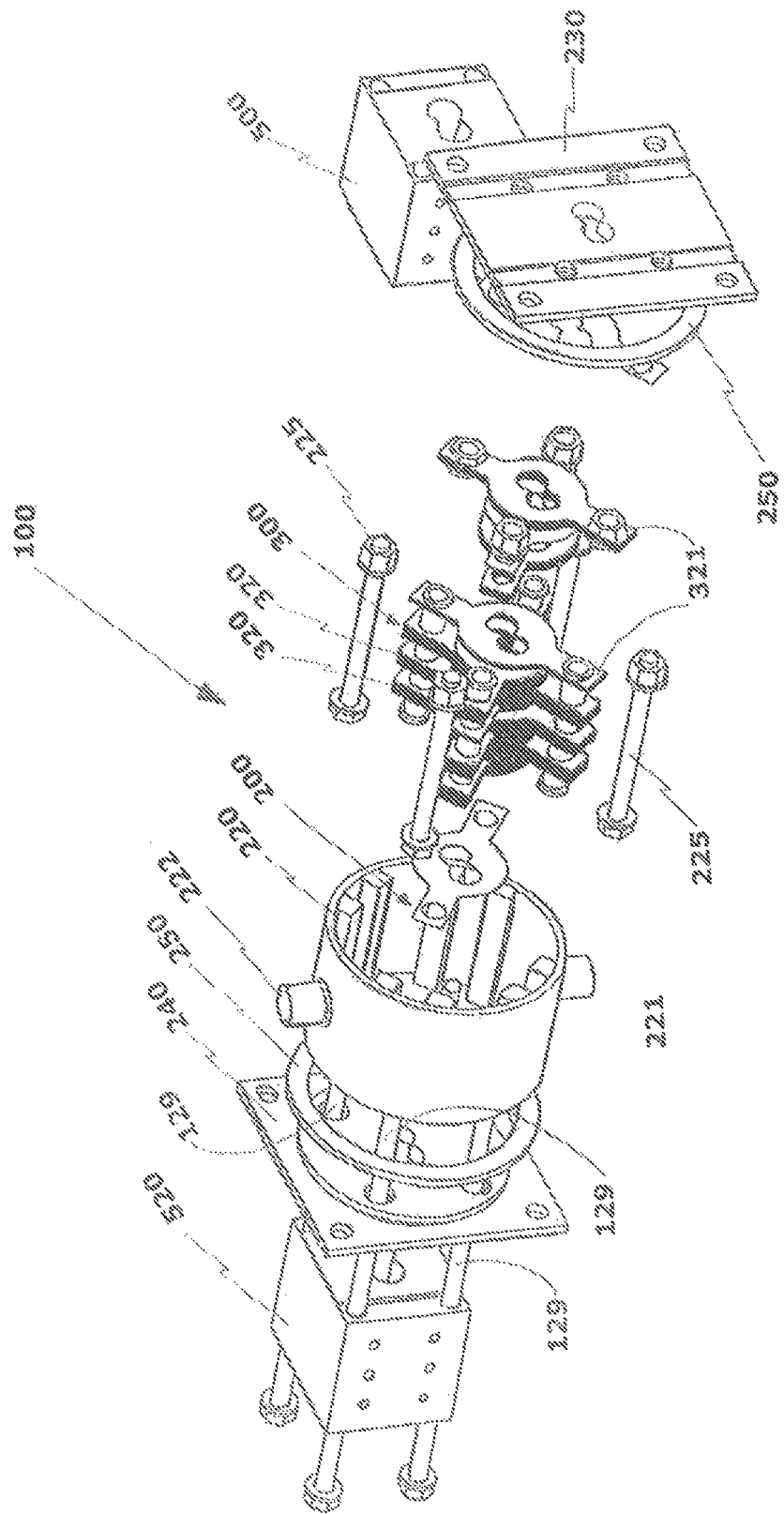
FIG. 2 schematically illustrates an embodiment of a twin screw extruder solid/fluid separation module in exploded view.

One embodiment of a membrane-free solid/fluid separator module 100 in accordance with the invention is shown in FIGS. 2 and 3, which module is capable of withstanding very high internal pressure forces (up to 5000 psig). This solid/fluid separator module can be used with the process and apparatus shown in FIG. 1 while being able to control the permeability/porosity (filtration capability) by various filter plate configurations and plate thicknesses as required by the type of biomass/solids treated.

In one embodiment, as illustrated in FIG. 2, a solid/fluid separation module 100 is used in association with a screw press and mounted between the twin screw extruder barrel 500 and extruder block 520 of the screw press. The module 100 separates fluids (liquid and/or gas) from a liquid containing mass of solids compressed by the screw press, preferably to pressures above 100 psig. The separation module 100 includes a collection chamber 200 and a filter unit 300 having a porosity of 5% to 40% (total pore area relative to the total filter surface). Preferably, the module 100 withstands operating pressures up to 5000 psig at a filter porosity of 5 to 40%, more preferably 11 to 40%. The filter unit 300 preferably includes a plurality of filter pores with a pore size of 0.00003 to 0.005 square inch.

In a preferred embodiment, the filter unit 300 includes filter pores having a pore size of 0.00005 square inch for the separation of fine solids, a porosity of 5.7% and a pressure resistance of 2,500 psig. In another embodiment, the filter unit 300 includes filter pores having a pore size of 0.005 square inch and a porosity of 20% and a pressure resistance of 5,000 psig. In a further preferred embodiment, the filter unit 300 includes filter pores of a pore size of 0.00005 square inch and a porosity of 11.4%. In still another preferred embodiment, the filter unit 300 includes filter pores having a pore size of 0.005 square inch and a porosity of 40%.

The basic construction of the separation module 100 is shown in FIGS. 2 and 3. A collection chamber 200, which is capable of withstanding the highest pressure of any component is used to separate the filtered out fluids into gases and liquid. The collection chamber is defined by a pressure jacket or housing 220 and intake and output end plates 230 and 240. Liquid can be drained from the collection chamber 200 through a liquid drain 221, preferably located at the lowest point on the pressure jacket 220. The pressure jacket 220 further includes a plurality of alignment ridges 223 extending parallel to a longitudinal axis of the jacket on the inside of the jacket, for alignment of the filter and backer plates within the collection chamber 200. Gas accumulated in the collection chamber 200 can be exhausted from the chamber through a gas drain 222, preferably located at the highest point on the pressure jacket 220. The high pressure collection chamber 200 is sealed by way of circular seals 250 positioned between axial ends of the pressure jacket 220 and the end plates 230, 240. This high pressure/high temperature capability allows for washing of biomass with fluids such as ammonia, CO2 and water which are normally in the gaseous state at process operating temperatures of 50 to 250° C. pressures. The separation module is fastened together by assembly bolts 225 located outside the pressure jacket 220 for pulling the end plates 230, 240 together and clamping the pressure jacket 220 and circular seals 250 therebetween. Filter unit clamping bolts 129 (see FIG. 2) can also be used to clamp together the filter packs 321, 322 in the filter unit 300. In a preferred embodiment, the filter unit clamping bolts extent through the end plates 230, 240 and provide for additional clamping together of the separation module 200. The filter unit clamping bolts 129 can also extend through the extruder block 520 for fastening of the extruder block to the separation module. However, to minimize the number of penetration points in the separation module 200 which need to be reliably sealed for maintaining a pressure in the collection chamber 200, the filter unit fastening bolts 129 are omitted and all clamping together of the pieces of the separation unit is achieved by fastening structures, such as bolts 225, located outside the pressure jacket. Depending on the pressures used, some gases can be separated right in the collection chamber 200, or in some circumstances (as shown in FIG. 1) a separate flash vessel can be utilized to optimize the overall efficiency of the process.

The filter unit 300 includes several plate blocks 320 assembled from a stack of the basic filter packs 321, 322 of the invention, the combination of a filter plate 120 placed against a backer plate 160, 180, which are described in more detail below with reference to FIGS. 4 to 12. There are right hand filter packs 321 including a filter plate 120 and a right hand backer plate 160, and left hand filter packs 322 including a filter plate 120 and a left hand backer plate 180.

In one aspect, the separation module includes a pressurizable collection chamber 200 and a filter unit 300 for sealingly receiving the pressurized mass (not shown). The filter unit 300 has a preselected filter pore size and a preselected porosity. The filter unit 300 includes at least one filter plate 120 having opposite front and back faces 121, 123, a cover plate 230 engaging the front face 121 of the filter plate 120 and a backer plate 160, 180 engaging the back face 123 of the filter plate 120. The filter, cover and backer plates (120, 230, 160/180) define a throughgoing core opening 128 sealed from the collection chamber 200 for receiving the pressurized mass (not shown). The filter plate 120 has at least one throughgoing filter slot 132 extending away from the core opening 128 into the filter plate, the filter slot 132 being sealed at the front and back faces 121, 123 by the cover and backer plates 230, 160/180, for forming a filter passage having the preselected filter pore size. The backer plate 160/180 has a recess 164 for defining together with the back face 123 a drainage passage in fluid communication with the collection chamber 200 and the filter slot 132 (see FIGS. 11 and 12). For increased porosity, the filter plate 120 preferably includes a plurality of separate filter slots 132 and the drainage passage 164 is in fluid communication with all the filter slots 132. To increase the porosity of the filter unit even further, the filter unit preferably includes multiple pairs of filter and backer plates (120, 160/180) arranged behind the cover plate 230 in a stack of alternating filter and cover plates, whereby each backer plate 160/180 sandwiched between two filter plates 120 functions as the backer plate for one filter plate and as the cover plate for the other filter plate. By alternating the filter and backer plates (120, 160/180), the separating pressure capacity of the filter unit 300 is increased. By using backer plates 160/180 which are thicker than the filter plates 120, the pressure capacity of the filter unit 300 can be further improved.

In the embodiment of FIG. 2, the separation module 100 is mounted to the barrel 500 of a screw press and the core opening 128 is sized to fittingly receive a portion of the press screw (not shown). The press screw of a screw press generally has very close tolerances to the core opening 128 of the filter block 300 and continually scrapes the compressed material away from the filter surface while at the same time generating significant separating pressures. In the event that a small amount of fibers become trapped on the surface of the filter, they will be sheared by the extruder screws into smaller pieces and ultimately pass through the filter and out with the liquid stream as very fine particles. This provides a solid/fluid separation device which allows for the separation of solid and liquid portions of a material in a high pressure and temperature environment.

By having the extruder screw swipe the filter pores 134 tangentially, the separation device is less susceptible to clogging. Due to the elevated porosity and pressure resistance of the separation module 100 in accordance with the invention, a dry matter content in the dry portion discharge of up to 90% is possible, while at the same time a relatively clean liquid portion is achieved, due to the small pore size, with suspended solids being as low as 1%. It will be readily understood that the solid/fluid separation module in accordance with the invention can be used in many different applications to separate solid/fluid portions of a material.

In pilot testing on a continuous basis, 100 g units of biomass containing 40 g of solids and 60 g of water were washed with 40 g of water and then the liquid was squeezed out the filter using 600 psig internal force at a temperature of 100 C to obtain a dry biomass discharge (solids portion of the liquid/solid biomass) containing 39 g of suspended solids and 5 g of water. The filtrate containing 95 g of water was relatively clean containing only 1 g of suspended solids with mean particle size of 5 microns and a particle distribution as per FIG. 13.

Further, as the solid/fluid separation device of the present invention is less susceptible to clogging, there is less need for maintenance as is periodically required with known separation devices. Thus, the solid/fluid separation device can be used in a process with less downtime and less maintenance resulting in increased production capability and less cost.

FIG. 4 shows a fine filter plate 120 having a circular middle section 122 attached to a first support tab 124 and a second support tab 126. The circular middle section 122 has a figure eight shaped core opening 128 for fittingly receiving the press screws of a twin screw press. The filter plate 120 has a front face 121 and a back face 123. The core opening 128 is surrounded by a plurality of fine fingers 130 and intermediate filter slots 132. To achieve maximum solid/fluid separation efficiency, it is desirable to minimize filter pore size, while maximizing filter. Minimizing pore size is a challenge in conventional screw presses due to the need for cutting cylindrical passages into the filter jacket. This problem is addressed with a filter unit in accordance with the invention, wherein filter pores are formed by simply cutting a slot 132 into a thin filter plate 120. The filter slot 132 is cut though the full thickness of the plate 120 and is thus referred to herein as a throughgoing slot. Very small filter pores can be achieved with filter plates 120 in accordance with the invention by using very thin filter plates 120 and very fine slots 132 as shown in FIGS. 4 and 5. For example, by using a filter plate of 0.005 inch thickness and cutting a slot of 0.01 inch width into the filter plate, a pore size of only 0.00005 square inch can be achieved. For even finer filtering, a filter plate of 0.003 inch thickness is used with a filter slot width of 0.01 inch, resulting in a pore size of only 0.00003 square inch.

As shown in FIG. 5, the very fine slots 132 and intermediate fine fingers 130 are shaped and positioned so that they provide filter slots that extend from the core opening 128 into the filter plate 120 and towards an outer portion of the middle section 122. Preferably, the ends of the filter slots 132 are all located on a circle concentrical with and spaced inwardly from an outer edge of the circular middle section 122. To improve liquid flow through the fine drainage channels, the channels are narrower at their inner end 134 into the core opening 128 and flare outwardly to their outer end 136.

Figure 7:
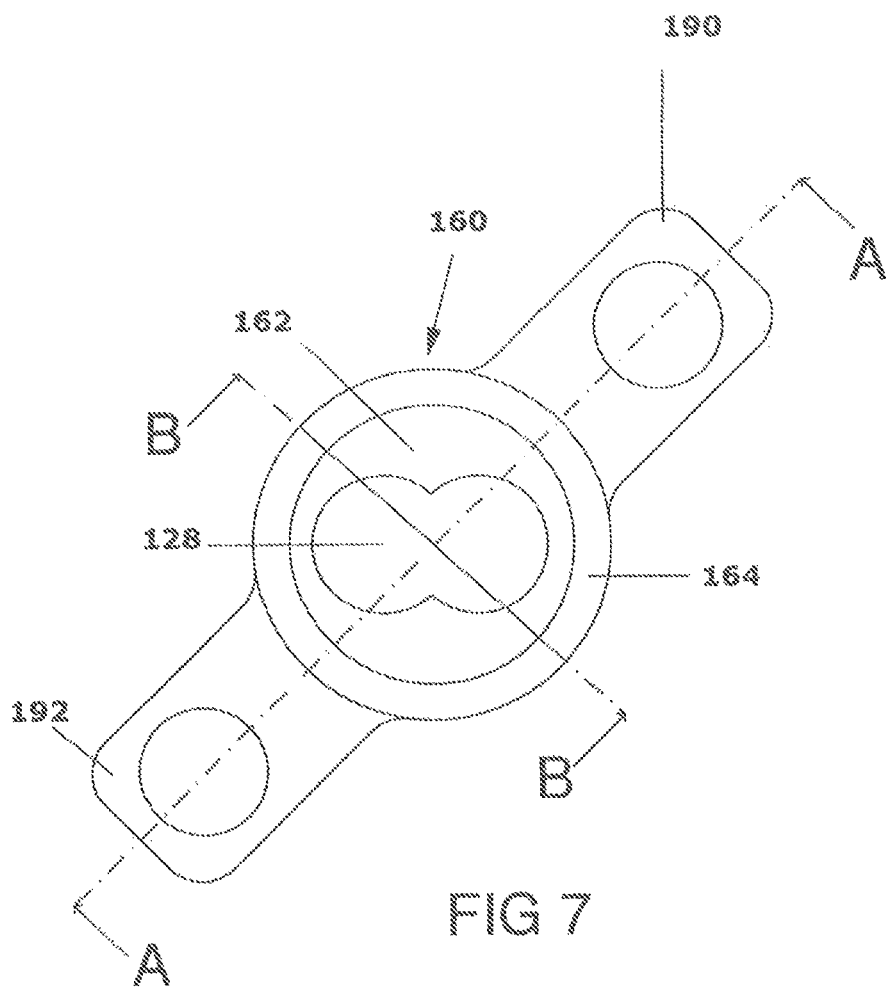
FIG. 7 shows a right hand backer plate of the embodiment of FIG. 3
Figure 8:
FIG. 8 is a cross-sectional view of the backer plate of FIG. 7, taken along line B-B.
Figure 9:
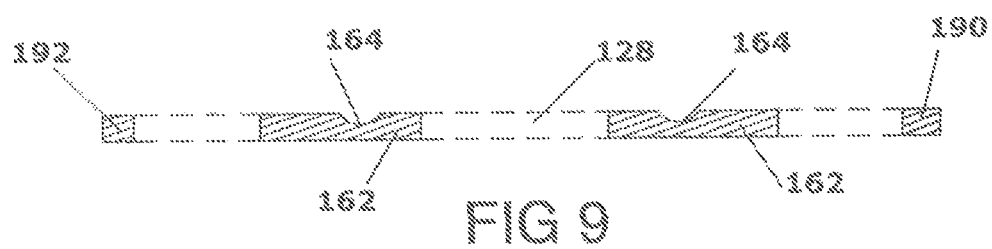
FIG. 9 is a cross-sectional view of the backer plate of FIG. 7, taken along line A-A.
Figure 10:
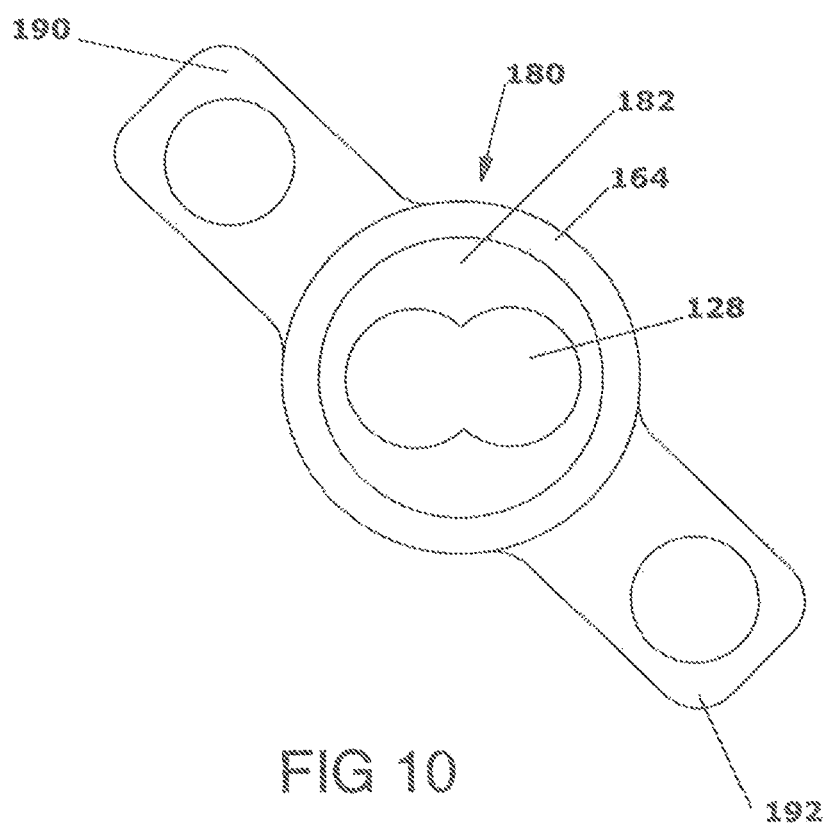
FIG. 10 shows a left hand backer plate of the embodiment of FIG. 3.
Figure 11:
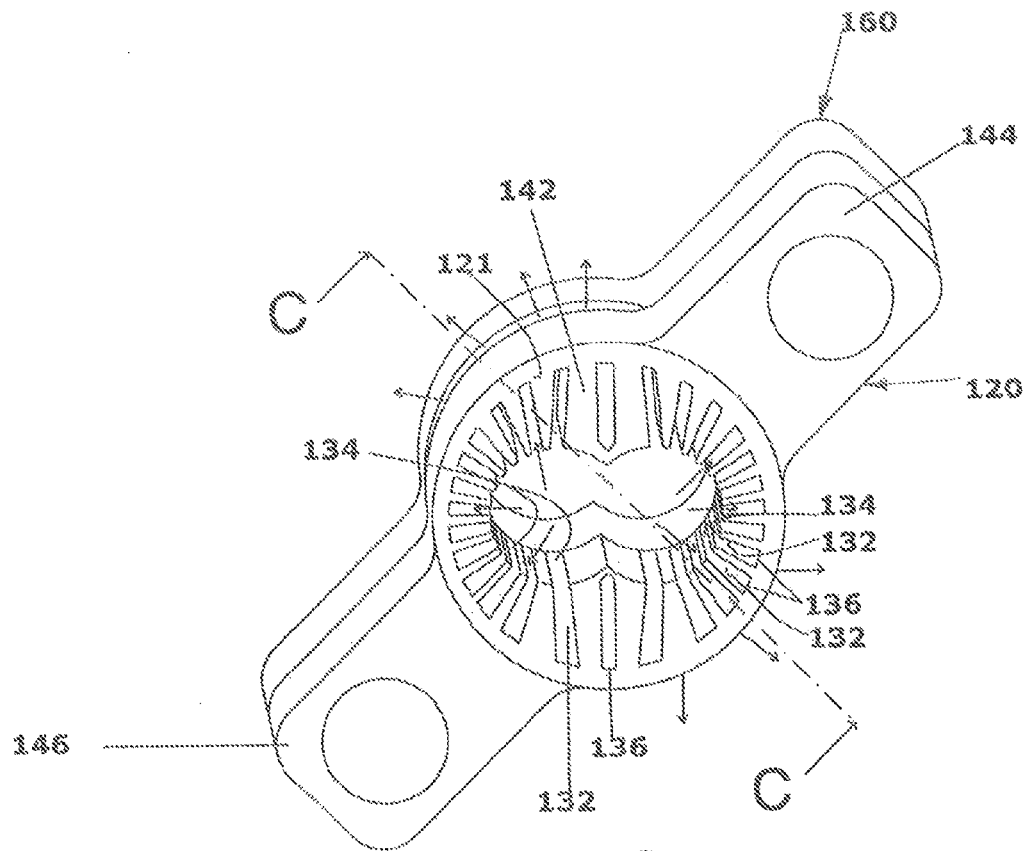
FIG. 11 is an isometric view of a pair of filter and backer plates in accordance with FIGS. 6 and 7.
Figure 12:
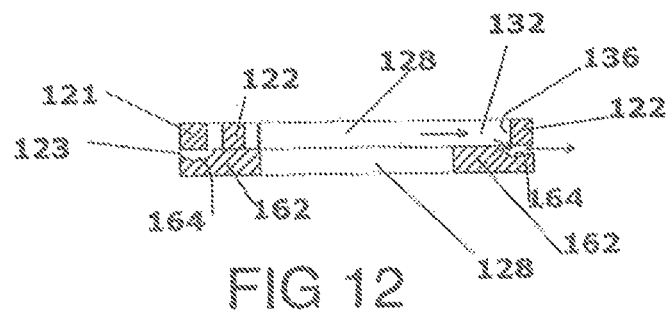
FIG. 12 is a cross-sectional view of the pair of filter and backer plates of FIG. 11, taken along line C-C.
Figure 13:
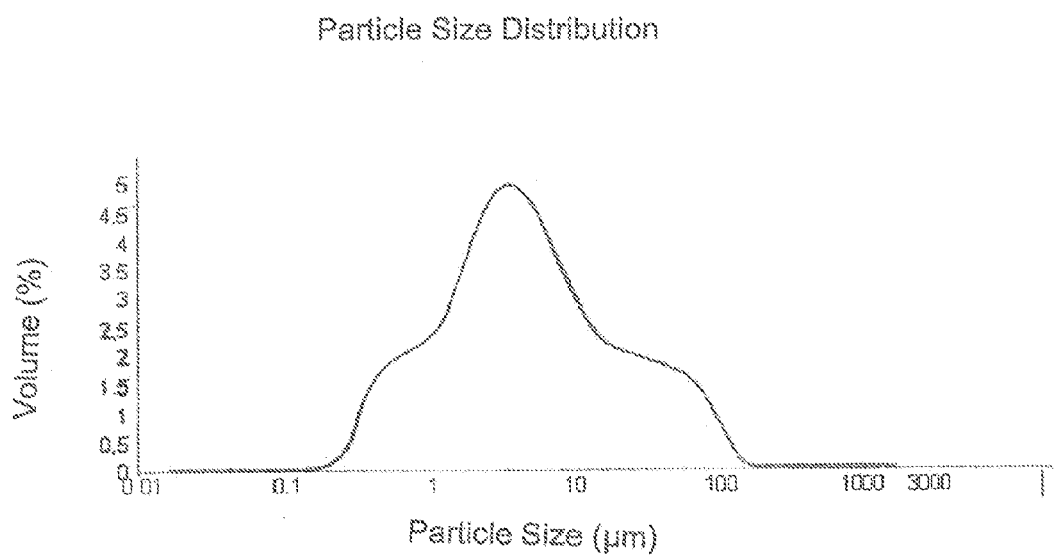
FIG. 13 shows the particle size distribution of the particles found in a filtrate obtained with one embodiment of the separation module.

The filter plate 120 is positioned against a backer plate as shown in FIGS. 11 and 12. This will be discussed in more detail further below. There are two types of backer plates, left hand backer plates 160 as shown in FIG. 7 and right hand backer plates 180 as shown in FIG. 10. The left and right hand backer plates 160, 180 have the same principle construction and include a circular central portion 162, 182 with the core opening 128 and mounting tabs 190, 192 extending from the central portion 162, 182. The only difference between the left and right hand backer plates is the orientation of the mounting tabs 190, 192 in relation to the core opening 128, with the tabs extending at a 45 degree angle to the right, relative to the transverse axis of the core opening 128 in the right hand backer plate 160 and at a 45 degree angle to the left in the left hand backer plate 180. Left and right handed backer plates are thereby used to create a 90 degree shift in the holding pattern of the plates and to provide a means for liquid to drain to the bottom of the collection chamber and gases to flow to the top of the collection chamber if the particular biomass requires liquid/gas separation at this stage. The number of consecutive right hand plates (or conversely left hand plates) with intermediate filter plates is usually equal to at least 0.25" thick but can be as much as 1" thick depending on the overall number of plates.

The filter plate mounting tabs 124, 126 and the backer plate mounting tabs 190, 192 are all shaped to be fittingly received between pairs of alignment ridges 223 mounted on an inner wall of the pressure jacket 220. Each type of backer plate has a machined peripheral groove 164 on the central portion 162, 182 as is apparent from FIGS. 7 to 9 and 10, the cross-sections through the left handed backer plate 180 being identical to those of the right handed backer plate 180 shown in FIGS. 8 and 9. The peripheral groove 164 is positioned to correspond with the outer ends 136 of the filter slots 132 in the filter plate 120 (see FIGS. 4-6), when the filter plate 120 and backer plate 160, 180, are positioned back to back with the core opening 128 aligned as shown in FIGS. 11 and 12.

FIGS. 11 and 12 illustrate the most basic filter pack in accordance with the invention, a filter plate 120 and a backer plate 160 engaging the rear face 123 of the filter plate. Fluids (liquid and/or gas) entrained in the pressurized mass (not illustrated) fed through the core opening 128 is forced by the separating pressure present to flow into the filter slots 132 (see arrows). At the end 136 of the filter slot, the fluid is redirected to flow into the peripheral groove 164 in the backer plate 160 and exits the peripheral groove 164 into the collection chamber (see FIGS. 11, 12 and 3). As such, the fine filter plate 120 can filter out liquid and very small particles which travel through the filter slots 132 in a direction transverse to the flow of biomass through the figure eight shaped core opening 128.

Figure 6:
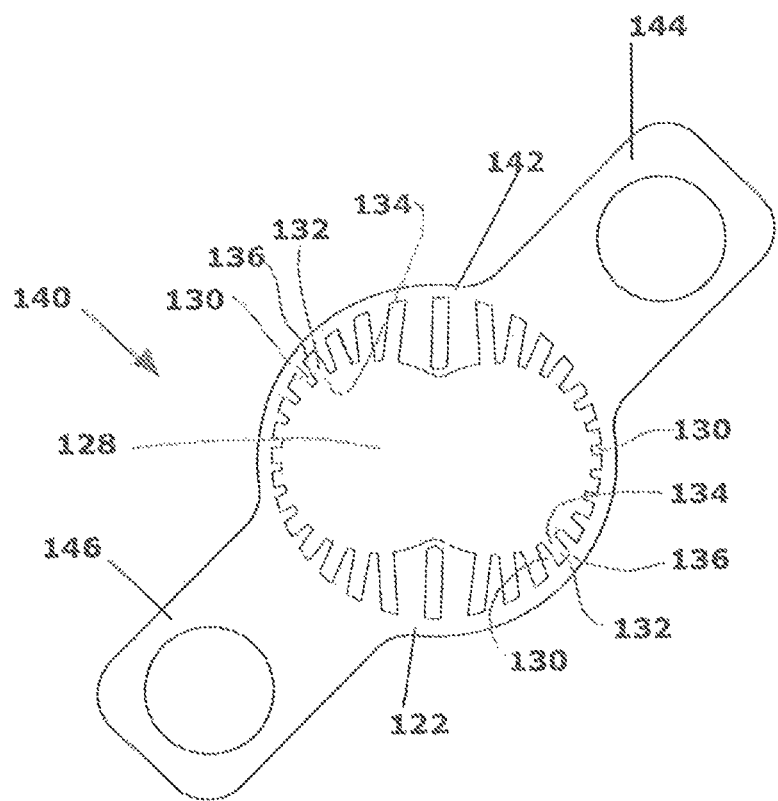
FIG. 6 shows a filter (finger) plate of the separation module having wider filter slots than the embodiment of FIGS. 4 and 5.

Conversely with a larger pore plate configuration, such as that shown in FIG. 6, which is suitable for larger particles/cellulose biomass fibers, the limiting factor on porosity is the plate thickness of the filter plate. It has been found with cellulose biomass that this coarser filter plate configuration provides good solid-liquid separation, while at the same time minimizing the surface area and number of plates required to achieve the same liquid separation with the same internal pressure as with the fine filter plate of FIG. 4.

As shown in FIG. 6, a larger pore, coarse filter plate 140 has a circular middle filter section 142 attached to a first support tab 144 and a second support tab 146. The circular middle filter section 142 has a figure eight shaped core opening 128 defined by a plurality of larger fingers 130 between filter slots 132 cut through the filter plate 140. As shown in FIG. 6, the larger fingers 130 are positioned between coarse drainage channels 132.

The coarse filter plate 140 is positionable against a backer plate, such as the left hand backer plate 160 shown in FIG. 7 to achieve a filter pack as shown in FIGS. 11 and 12.

Overall, with the higher pressure capability, either more liquid can be squeezed from the solids or, for the same material dryness, a higher production rate can be achieved per unit filtration area.

The quality of filtration (solids capture) can be controlled depending on plate configurations and thicknesses. The filtration/pressure rating/capital cost can be optimized depending on the filtration requirements of the particular biomass. The plate configurations can be installed in an extruder (single, twin or triple screws) to develop high pressure, high throughput, continuous separation. The solid/fluid separation module is self cleaning (for twin and triple screws) due to the wiping nature of the screws and the cross axial flow pattern. The filtration area is flexible depending on process requirements as the length of plate pack can be easily custom fit for the particular requirements. The module can be used to wash solids in a co current or counter current configuration in single or multiple stages in one machine reducing capital cost and energy requirements. The pressure of the liquid filtrate can be controlled from vacuum conditions to even higher than the filter block internal pressure (2,000 to 3,000 psig) if required. This provides great process flexibility for further separations in the liquid stream (example super critical $CO_2$ under high pressure, ammonia liquid used for washing under high pressure, or release of VOC and ammonia gases in the liquid filtrate chamber using vacuum). The high back pressure capability (higher than internal filter block pressure) can be used to back flush the filter during operation in case of pluggage or scaling of the filter minimizing down time.

Fine Filter Porosity

The size of the fine pores is the thickness of the fine plate× the width of the slot at opening. In the filter plate of FIG. 4, the pore size is 0.005" (thickness of the plate)×0.010" (width of the slot at the opening)=0.00005 square inch per pore. There are 144 pores per plate for a total pore area of =0.0072 square inch open area per plate.

In an experimental setup using a small, 1 inch diameter twin screw extruder, this finger plate was paired with one 0.020" thick backer plate, resulting in a total filter area of 0.1256 square inches. Therefore the total open area of this one set of the experimental plates (filter pack) calculated as 0.0072/0.1256=5.7%. At this porosity, the pair of experimental plates (0.020" thick backer plates) was able to withstand a separation pressure of 2,500 psig. A 1" thickness pack of experimental plates included 40 filter plates in total×0.0072 square inch=0.288 square inch of open area. That equals to more than a 0.5" diameter pipe, all achievable within a distance of only 1 inch of extruder length in the small 1" diameter extruder used.

Coarse Filter Porosity

In the experimental coarse filter plate used, as shown in FIG. 6, in terms of filtering capability and liquid flow path, the width of the filter slots was basically the same as the thickness of the filter plate, resulting in a series of axial grooves. The total open area of one set of plates (coarse filter plate+backer plate) is a ratio of the plate thickness which in this case=0.005/0.025=20% or about 4 times the open area of the fine filter plate system. Using coarse plates in a 1" thickness pack of plates, at 40 finger plates in total, we ended up with 40×0.0209 square inch open area per plate=0.837 square inch of open area. This is larger than a 1" diameter pipe, all achieved within a distance of 1 inch of extruder length in the small 1" diameter extruder used.

For both types of plates, the porosity can be significantly increased by decreasing the thickness of the backer plates, while keeping the filter plate at the same thickness. Reducing the backer plate thickness by 50% will double the porosity of the filter unit. Meanwhile, the strength of the filter unit will decrease whenever the backer plate thickness is decreased, but this can be counteracted by increasing the overall diameter of the backer plates, making the liquid flow path slightly longer but keeping the open area the same.

The use of filter plates 120 for the manufacturing of the filter module allows for low cost production of the filter, since low cost production methods can be used. The plates can be laser cut, or for coarser filtration the plates can be stamped. The overall equipment cost for biomass pretreatment is also lower due to the capability of having multiple process steps occurring in a single machine. The solid/fluid separation module can accommodate three-phase separation simultaneously.

The type of material used for the manufacture of the filter unit can be adapted to different process conditions. For example, in low pH/corrosive applications materials like titanium, high nickel and molybdenum alloys can be used.

In particular, the inventors have developed a solid/fluid separation device which separates solid and liquid portions of a material and is less susceptible to clogging versus known solid/fluid separation devices. It is contemplated that the solid/fluid separation device can be used in many different applications to separate solid/fluid portions of a material. Further, as the solid/fluid separation device of the present invention is less susceptible to clogging, there is less need for maintenance including back washing as is periodically required with known devices. Thus, the solid/fluid separation device can be used in a process with less downtime and less maintenance resulting in increased production capability and less cost.

In the solid/fluid separation device described, the screw elements that transfer the material internally in the separation device have very close tolerances to the internal surface of the filter block and continually scrape the material away from the filter surface. In the event that a small amount of fibers became trapped on the surface of the filter, they will be sheared by the extruder elements into smaller pieces and ultimately pass through the filter and out with the liquid stream.

The total number of plate pairs (finger and backer plates) can vary depending on the biomass and controls the overall filter area. For the same liquid separation conditions, more plates/more surface area is required for smaller pores. The size of the pores controls the amount of solids which pass to the liquid portion. Each biomass has a need for a certain pore size to obtain a certain solids capture (amount of suspended solids in liquid filtrate).

Although this disclosure has described and illustrated certain embodiments, it is also to be understood that the system, apparatus and method described is not restricted to these particular embodiments. Rather, it is understood that all embodiments, which are functional or mechanical equivalents of the specific embodiments and features that have been described and illustrated herein are included.

It will be understood that, although various features have been described with respect to one or another of the embodiments, the various features and embodiments may be combined or used in conjunction with other features and embodiments as described and illustrated herein.

What is claimed is:

1. A solid/fluid separating module for separating a pressurized mass of fluid containing solids, comprising
a pressurizable collection chamber and at least one filter unit for separating fluid from the pressurized mass and guiding the fluid into the collection chamber;
the filter unit defining a core opening sealed from the collection chamber for receiving the pressurized mass and including a filter pack consisting of a filter plate having front and back faces and a filter slot cut through the plate from the front face to the back face and extending from an inner end at the core opening to a closed outer end in the filter plate for directing fluid away from the core opening; and a backer plate for guiding fluid collected in the filter slot from the filter slot into the collection chamber.

2. The separating module of claim 1, wherein the filter plate includes a plurality of filter slots.

3. The separating module of claim 1, wherein the filter unit has a plurality of filter packs stacked back to back to form a filter block including a stack of alternating filter and backer plates and defining the core opening.

4. The separating module of claim 1, wherein the filter unit has a preselected filter pore size and the filter slot defines an opening area at the inner end corresponding to the preselected pore size.

5. The separating module of claim 3, wherein the filter unit has a preselected filter pore size and a preselected porosity, each filter slot defining an opening area at the inner end corresponding to the preselected pore size and each filter pack having a porosity calculated from a total surface of the core opening, the preselected pore size and the number of filter slots, the filter unit including a number of filter packs at least equal to the preselected porosity/filter pack porosity.

6. The separating module of claim 1, wherein the filter slot widens in a direction away from the core opening.

7. The separating module of claim 1, wherein the collection chamber has a pressure jacket for housing the filter unit, the pressure jacket being sealably closed at an input end by an input end plate and at an output end by an outlet end plate, the filter pack being sandwiched between the input and outlet end plates.

8. The separating module of claim 7, wherein the pressure jacket includes separate drains for liquids and gases.

9. The separating module of claim 7, wherein the filter unit has a plurality of filter packs stacked back to back to form a filter block including a stack of alternating filter and backer plates sandwiched between the input and outlet end plates.

10. The separating module of claim 9, wherein each filter plate includes a plurality of the filter slots.

11. The separating module of claim 10, wherein the backer plate has a recess for defining, together with a back face of the filter plate, a drainage passage in fluid communication with the collection chamber and the filter slot.

12. A solid/fluid separating module for use with a screw extruder having an extrusion barrel, an extruder block and a rotatable extruder screw fittingly received in the extruder barrel, the separating module comprising:
a pressurizable collection chamber connectable at an input end to the extruder barrel and at an outlet end to the extruder block and having a pressure jacket sealably closed at an input end by an input end plate and at an output end by an outlet end plate; and
at least one filter pack in the collection chamber defining a core opening sealed from the collection chamber for communication with the extruder barrel and extruder block, the filter pack including at least one filter plate having front and back faces and a throughgoing filter slot cut through the plate from the front face to the back face and extending from the core opening into the filter plate to a closed end, for directing fluids away from the core opening and at least one backer plate defining, together with a back face of the filter plate, a drainage passage in fluid communication with the filter slot and the collection chamber, for draining fluids collected in the filter slot from the filter slot into the collection chamber, the filter pack being sandwiched between the input and outlet end plates, the inlet, outlet, filter and backer plates defining the core opening, for communicating with the extrusion barrel, the filter plate having at least one filtering passage communicating with and extending away from the core opening, the backer plate having a recess for guiding liquid in the filter passage into the collection chamber, and the collection chamber having a drainage outlet for draining liquids separated by the filter pack.

* * * * *